(12) United States Patent
Shimizu et al.

(10) Patent No.: US 6,445,183 B1
(45) Date of Patent: Sep. 3, 2002

(54) MAGNETIC RESONANCE IMAGE DIAGNOSING APPARATUS

(75) Inventors: Hiromichi Shimizu, Tokyo; Shigeru Watanabe, Kitasoma-gun, both of (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/857,304
(22) PCT Filed: Dec. 3, 1999
(86) PCT No.: PCT/JP99/06797
§ 371 (c)(1),
(2), (4) Date: Jul. 30, 2001
(87) PCT Pub. No.: WO00/32107
PCT Pub. Date: Jun. 8, 2000

(30) Foreign Application Priority Data

Dec. 3, 1998 (JP) .......................................... 10-344401

(51) Int. Cl.$^7$ ................................................. G01V 3/00
(52) U.S. Cl. ........................ 324/309; 324/315; 324/322
(58) Field of Search ................................ 324/309, 307, 324/315, 322; 600/410, 412; 128/736, 653

(56) References Cited

U.S. PATENT DOCUMENTS 5,711,300 A * 1/1998 Schneider et al. .......... 128/653
5,916,161 A * 6/1999 Ishihara et al. ............. 600/410

OTHER PUBLICATIONS

"Proton Resonance Shift of Water in the Gas and Liquid States", J.C. Hindman, Journal of Chemical Physics, vol. 44, pp. 4582–4592, Jun. 15, 1966.

* cited by examiner

*Primary Examiner*—Edward Lefkowitz
*Assistant Examiner*—Brij B. Shrivastav
(74) *Attorney, Agent, or Firm*—Antonelli, Terry, Stout & Kraus, LLP

(57) ABSTRACT

A burst wave 91 is applied as an RF magnetic filed in order to excite nuclei of hydrogen, and also a oradient magnetic field 95 along a readout direction is applied so as to excite magnetization in a stripe shape. Thereafter, while a magnetization-inverting RF magnetic field pulse 92 for selecting a slice is applied and a readout gradient magnetic field 96 is applied, a signal 97 is measured. At this time, a time instant when a spin echo is produced is made different from a time instant when a gradient magnetic field echo is produced, so that a phase rotation made by a chemical shift may be reflected on to a signal. The MR signal 97 is processed by a 2-dimensional Fourier-transform, and a phase distribution is calculated from both a real part and an imaginary part of complex data after the 2-dimensional Fourier-transform. Then, this calculated phase distribution is converted into a temperature change so as to display the temperature change. A temperature change in a diseased portion in connection with IVMR can be monitored in real time.

25 Claims, 5 Drawing Sheets

FOURIER TRANSFORM

MAGNETIC RESONANCE IMAGE DIAGNOSING APPARATUS

TECHNICAL FIELD

The present invention relates to a magnetic resonance diagnosing apparatus (MRI), and more specifically, to a medical MRI apparatus suitably for measuring a temperature distribution.

BACKGROUND ART

Very recently, MRIs may constitute very important diagnosing means for diseases as diagnostic imaging apparatus capable of drawing tissues under superior conditions in conjunction with X-ray CT. Furthermore, MRIs are not only used in diagnosing purposes, but also are developed as such a technique (Interventional MR, namely IVMR) which is applied to guides for catheters and laser fibers when low invasive medical treatments are carried out. As one of these MRI applications, a temperature distribution of a tissue is detected. This MRI application is attractively known as such a means for monitoring curing conditions of a diseased portion in a real time manner while a laser ablation and/or a focused ultrasonic ablation is carried out, during which a tissue of such a diseased portion as tumor and hernia is burned out so as to be cured.

Among parameters for defining a magnetic resonance signal (MR signal), such a parameter indicative of a temperature dependent characteristic involves the spin density "ρ", longitudinal relaxation time "T1", the transverse relaxation time "T2", the diffusion coefficient of water, the chemical shift "94" of water proton, and the like (see J. C. Hindman, J. Chem. Phys. Volume 44, page 4582, 1966). Among these parameters, it is known that the reliability of chemical shift of water proton is high, in view of less dependent characteristics to the factors except for the temperature.

As a utilization method of a chemical shift, a method for employing a phase map is more effective, since spatial resolution is high and measurement time is short (see JP-A-5-253192 "A Precise and Fast Temperature Mapping Method Using Water Proton Chemical Shift" Y. Ishihara, A. Calderon et al., Abstracts of the Society of Magnetic Resonance Medicine, 11th Annual Meeting, Berlin, p. 4803 (1992)).

This method is performed as follows: That is, while using the sequence having the chemical shift sensitive characteristic such as the gradient echo (GrE) method, a change in the chemical shifts occurred before and after the temperature change is detected as the phase difference of the MR signal. The frequency shift of water proton caused by the temperature is equal to 0.01 ppm/° C., and the phase difference "$\Delta\phi$" is expressed by the following formula (1):

$$\Delta\phi = 2\pi \cdot \Delta\delta \cdot \gamma Bo \cdot TE \quad (1)$$

In this formula (1), symbol $\Delta\phi$ shows the phase difference in the pixel of interest, symbol $\Delta\delta$ represents a change in the chemical shifts of water proton in this pixel of interest, symbol "γ" denotes the gyromagnetic ratio, symbol Bo shows the static magnetic field strength, and symbol TE indicates the echo time. These symbols are similarly applied to the below-mentioned descriptions.

Further, the temperature difference $\Delta T$ is calculated from this phase difference $\Delta\phi$ based upon the following formula (2):

$$\Delta T(x, y) = \frac{\Delta\phi(x, y)}{2\pi \cdot \gamma Bo \cdot TE \cdot \alpha} \quad (2)$$

In this formula (2), symbol "α" indicates the temperature dependent characteristic of the chemical shift of water proton, i.e., [0.01 ppm/° C.]. This symbol is similarly applied to the below-mentioned explanations.

The measuring precision of the temperatures by this method may depend upon both the S/N ratio of the signal and the stability of the hardware, and is on the order of +1° C. to -1° C.

In the conventional phase map formation by employing the GrE method sequence, it is practically difficult to form the phase map within the short time, since the phase encode loop must be repeated along one direction of the space in the 2-dimensional measurement, and the dual phase encode loop must be repeated along two directions of the space in the 3-dimensional measurement. As one example, assuming now that the echo time TE=20 ms, the repetition time TR=30 ms, and the phase encode step number is 64 by way of the highspeed GrE method, approximately 2 seconds are required to form the image. Moreover, in order to execute the slice encode by 16 steps, 32 seconds are required. In a temperature measurement executed in IVMR, a temperature change of a diseased portion, which is caused by a focused ultrasonic medical treatment and the like must be monitored in the real time mode. Also, it is desirable to image several sheets of images per 1 second, and also it is preferable to display a 3-dimensional temperature distribution in combination with these images. However, as previously explained, in accordance with the conventional GrE method, these operations could not be realized.

Therefore, an object of the present invention is to provide such an MRI apparatus capable of forming/displaying a temperature distribution image within a very short time period.

DISCLOSURE OF THE INVENTION

To solve the above-explained problem, in accordance with the present invention, as a radio-frequency magnetic field used to excite water proton, a series of radio-frequency pulses (will be referred to as a "burst wave" hereinafter) is employed which is constituted by a plurality of sub-pulses. Also, such a gradient magnetic field echo is produced which owns a higher phase sensitivity characteristic than that of a spin echo. As a result, a phase map can be formed in very high speeds, and also a temperature distribution can be displayed in very high speeds.

It should be understood that as the highspeed imaging sequence with employment of the burst wave, the burst method is known (JP-B-6-34784). An MR image diagnosing apparatus of the present invention is featured by that while a sequence is executed which is made by modifying the sequence of this burst method, a gradient magnetic field echo is produced to which a phase rotation proportional to a chemical shift is applied, and thus, both a phase map and a temperature map may be acquired.

In other words, an MRI apparatus, according to the present invention, is featured by such a magnetic resonance image diagnosing apparatus comprising: magnetic field generating means for generating a static magnetic field, a gradient magnetic field, and a radio-frequency (RF) magnetic field in a space where an object under examination is located; detecting means for detecting a magnetic resonance signal produced from the object under examination; means for reconstructing an image based upon the detected magnetic resonance signal; display means for displaying thereon an image; and control means for controlling each of the means, wherein:

the control means executes the below-mentioned sequences, namely:

1) a burst wave is applied as the radio-frequency magnetic field, and at the same time, the gradient magnetic field along at least one direction is applied;
2) a gradient magnetic field in the same direction as that of said gradient magnetic field is applied as a readout-operating gradient magnetic field, and an MR (magnetic resonance) signal is detected as a gradient magnetic field echo;
3) when the burst wave is applied, or the magnetic resonance signal is detected, such a gradient magnetic field which phase-encodes the magnetic resonance signal is applied;
4) the detected magnetic resonance signal is Fourier-transformed, and a phase distribution is calculated based upon both a real part and an imaginary part of complex data of the Fourier-transformed magnetic resonance signal; and
5) an image is constructed from the phase distribution or a temperature distribution obtained from the phase distribution, and the constructed image is displayed on the display means.

In this case, a burst wave will be referred to as "a series of RF pulses" which is constituted by employing a plurality of sub-pulses "p" as indicated in FIG. 3A. When a burst wave on a time axis is Fourier-transformed, a series of pulse stream having the same pulse number as that of the burst wave is obtained (see FIG. 3B) on a frequency axis. In this case, it is so assumed that an interval of the sub-pulses which constitute the RF burst on the time axis is equal to "u" (seconds) and also an entire length of the pulse stream is equal to "W" (seconds), an interval of rectangular waves which constitute the pulse stream on the frequency axis is equal to "1/u"(Hz) and a width thereof becomes "1/W"(Hz). Since the burst wave is used to excite a region 301 and the gradient magnetic field is applied thereto in this manner, this comb-shaped region 301 may be excited along the gradient magnetic field direction (namely, x direction in this drawing) as shown in FIG. 3C. Also, echoes whose number is equal to that of the RF pulses may be produced. Since different phase encodes are applied to these echoes, either a 2-dimensional phase distribution or a temperature distribution may be acquired by one shot. As a consequence, while either a phase image or a temperature distribution image is updated in real time in IVMR, these images may be displayed. Since the highspeed inversion of the gradient magnetic field is no longer required in this method, the image formations can be made in higher speeds, as compared with the EPI (Echo Planar Imaging) method capable of forming the 2-dimensional image by one shot.

Also, in accordance with the present invention, since the MR signals are measured as the gradient magnetic field echo which is produced by the diphase-rephase of spins, it is possible to acquire such data having the phase sensitivity characteristic.

In one mode of the present invention, after a burst wave has been applied, a magnetization-inverting radio-frequency magnetic field pulse is applied in combination with a slice-selecting gradient magnetic field. In this case, a gradient magnetic field echo is produced at a different time instant from such a time instant when a spin echo is produced by applying the magnetization inverting radio-frequency magnetic field pulse. Assuming now that a difference between the spin echo producing time instant and the gradation magnetic field echo producing time is "t0", such a phase rotation is applied to a signal, and this phase rotation is proportional to both this time difference "t0" and the chemical shift.

In the present invention, only the gradient magnetic field echo may be produced without producing the spin echo. In this case, the effective TE may be set to a long echo time, and also the phase sensitivity can be improved. It should be understood that since the slice selection by employing the magnetization-inverting radio-frequency magnetic field pulse cannot be carried out, this method is suitable for such a 3-dimensional measurement that the phase encode operation is carried out along the slice direction.

Also, in accordance with another mode of the present invention, a gradient magnetic field for a phase encode operation is also applied along the slice direction, the encode steps are repeated as to the slice direction so as to acquire data, so that a 3-dimensional phase distribution is formed. In this case, after the burst wave has been applied, the magnetization-inverting radio-frequency magnetic field pulse may be applied. Alternatively, the magnetization-inverting radio-frequency magnetic field pulse may not be employed.

In the case that the encode steps are repeated, while the frequency of the burst wave is changed every one cycle of the encode steps, different portions which are located in parallel to the read direction are excited, and also the excitating-purpose burst wave may be applied without waiting for the longitudinal magnetization recovery time.

As previously explained, since the burst wave is applied and also the gradient magnetic field along the readout direction is applied, the longitudinal magnetization along the read direction is excited in the comb-teeth shape (stripe shape), so that only a portion of the longitudinal magnetization is excited. As a consequence, when the excitation frequency is shifted and the longitudinal magnetization of the unexcited portion (302 in FIG. 3C) is excited, the subsequent excitation may be carried out after shorter waiting time than the normal TR has passed.

Also, in accordance with the present invention, the temperature distribution may be obtained as follows. That is, the phase distribution measurement is carried out at the different time instants two times, or more. The difference between these phase distributions is calculated, and this phase difference is converted into a temperature change. Then, the temperature distribution may be calculated from this temperature change. A temperature distribution image may be displayed in such a manner that a temperature difference is expressed by a color hue, gradation, or these combinations, while the normal temperature (for example, body temperature of object under examination) is used as a reference. The temperature distribution image may be preferably displayed by being superimposed on a tissue image. As a result, while such a tissue where a temperature change happens to occur is confirmed in colors and the like, the IVMR treatments may be advanced.

As previously explained in detail, in accordance with the present invention, since the imaging sequence employs the burst wave as the excitation-purpose radio-frequency magnetic field and this imaging sequence owns the high phase sensitivity, the 3-dimensional temperature distribution can be displayed in high speeds, and also, the safety aspects as to the IVMR operations under monitoring of MRI can be improved.

BEST MODE FOR CARRYING OUT THE INVENTION

Referring now to drawings, an MRI apparatus of the present invention will be described in detail.

Figure 4:
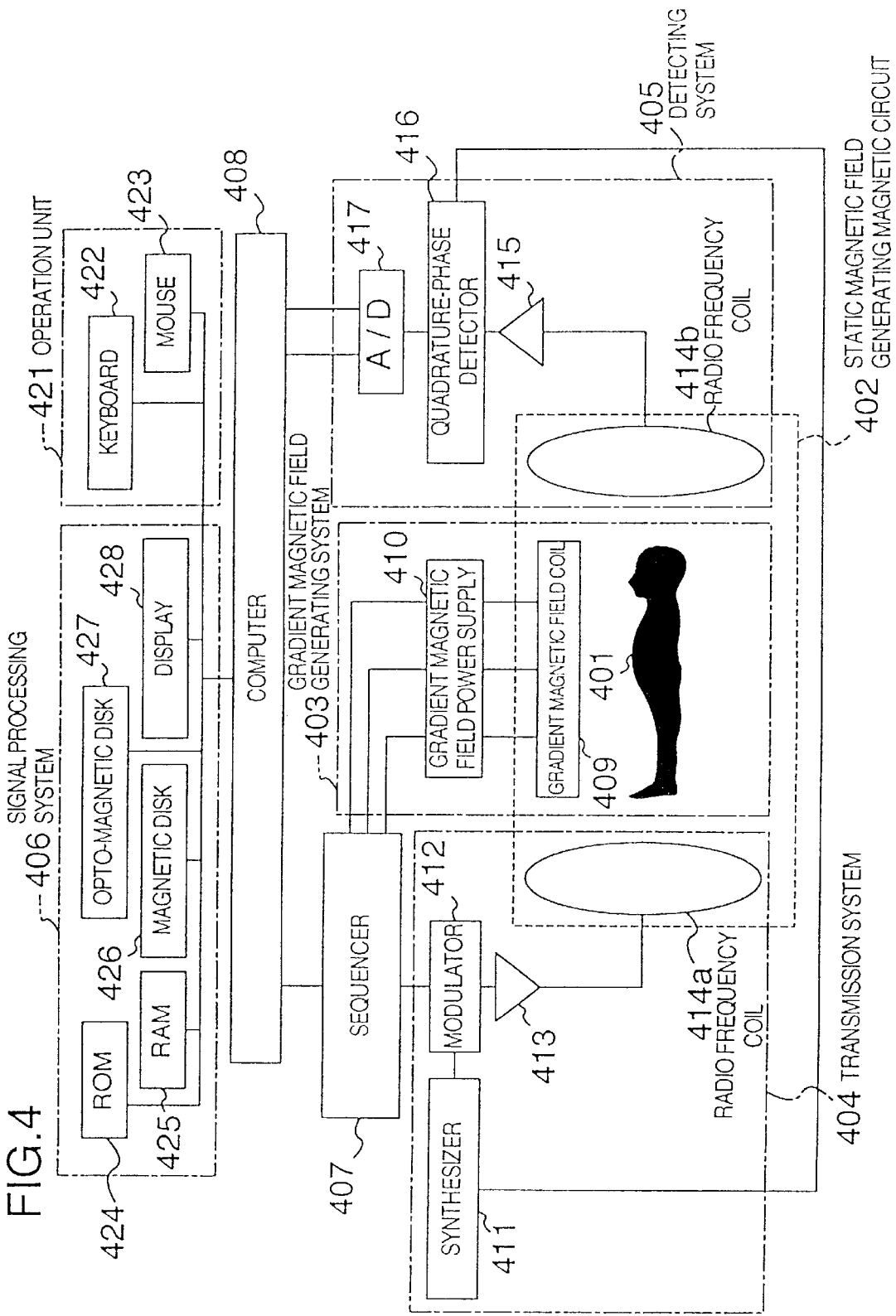
FIG. 4 is a diagram for representing an overall arrangement of an MRI apparatus to which the present invention is applied.

FIG. 4 is a schematic structural diagram of a magnetic resonance diagnosing apparatus to which the present invention is applied. This MRI apparatus is provided with a static magnetic field generating magnetic circuit 402, a transmission coil 414a, and a gradient magnetic field coil 409. The static magnetic field generating magnetic circuit 402 is equipped with either an electromagnet or a permanent magnet, which are used to generate a uniform static magnetic field B0 within an object under examination 401 as a magnetic field generating means. The transmission coil 414a generates an radio-frequency magnetic field. The gradient magnetic field coil 409 generates gradient magnetic fields Gx, Gy, Gz, the strengths of which are changed in a linear manner along three directions x, y, z located perpendicular to each other. The gradient magnetic field coil 409 is connected to a power supply 410 which supplies currents to the gradient magnetic field coil. Also, the MRI apparatus is provided with a detection coil 414b, a computer 408, a signal processing system 406, and an operation unit 421. The detection coil 414b detects MR signals produced from the object under examination 401 as a detection means. The computer 408 executes various calculations with respect to the MR signals so as to reconstruct an image. The signal processing system 406 is equipped with storage apparatus (424 to 427) for storing thereinto calculation results, and a display 428 for indication purposes. The operation unit 421 includes a keyboard 422 and a mouse 423, which are used to input data into the computer 408. As represented in the drawing, the coils 414a and 414b may be separately provided for transmission/reception operations. Alternatively, both these coils 414a and 414b may be commonly used.

Also, the computer 408 may function as a control means for controlling the respective magnetic field generating means and the detecting means, and may control through sequencer 407 the respective operations of the gradient magnetic field generating system 403 (namely, gradient magnetic field coil 409 and power supply 410 thereof), and of both the transmission system 404 and the detection system 405.

Next, operations of this apparatus will now be summarized. Radio-frequency (RF) signals produced by a synthesizer 411 is modulated by a modulator 412 under a timing controlled by the sequencer 407, the modulated radio-frequency signals are amplified by a power amplifier 413, and then the amplified radio-frequency signals are supplied to the transmission coil 414a. As a result, radio-frequency magnetic fields are produced within the object under examination 401 so as to excite nuclei spins. In the present invention, a series of radio-frequency pulses constituted by a plurality of sub-pulses, namely a burst wave is produced. Atomic nuclei to be investigated correspond to $^{31}P$ and $^{12}C$ other than $^{1}H$. In the temperature measurement according to the present invention, water protons are subjects to be measured.

On the other hand, the gradient magnetic field coil 409 is driven via the gradient magnetic field power supply 410, and the respective gradient magnetic fields along a slice direction, a phase encode direction, and a frequency encode direction are applied so as to select a region (slice) where nuclei spins are excited, and also so as to phase-encode and/or frequency-encode nuclear magnetic resonance signals generated therefrom.

An MR signal emitted from the object under examination 401 is received by the coil 414b, and after the received MR signal is amplified by the amplifier 415, the amplified MR signal is quadrature-detected by a dector 416. Then, the quadrature-detected MR signal is entered via an A/D converter 417 to the computer 408. After the computer 408 executes signal process operations of this quadrature-detected MR signal, this computer 408 displays images corresponding to a density distribution, a spectrum distribution, and the like on a CRT display 428. Based upon the density distribution of the nuclei spins and relaxation time thereof, contrast is applied to these density distribution and spectrum distribution. In the present invention, such information indicative of a phase image and/or a temperature distribution of a tissue is displayed by way of, for instance, a color display mode in addition to a tissue image corresponding to the density distribution of the nuclei spins. It should be noted that either data obtained while the computation is carried out or finally obtained data are stored in memories 424 and 425.

The above-described gradient magnetic field generation system 403, transmission system 404, and detection system 405 are controlled by the sequencer 407 in accordance with a pulse sequence which is determined based upon a measurement purpose. This sequencer 407 is controlled by the computer 408. In the present invention, the computer 408 may execute a sequence with employment of a burst wave, and also may acquire a phase distribution based upon a calculation of a detected MR signal. Furthermore, the computer 408 may execute a measurement for acquiring a phase distribution at two different time instants so as to acquire a temperature distribution of a tissue from a difference between the acquired phase distributions, and may display this temperature distribution on the CRT display 428.

Next, a description will now be made of an embodiment as to a temperature measurement according to the present invention with employment of such an apparatus with reference to FIG. 1 and FIG. 2. In this case, while a laser ablation of tumor is carried out as IVMR (Interventional MR), it is so assumed that a temperature of a diseased portion is monitored.

Figure 1:
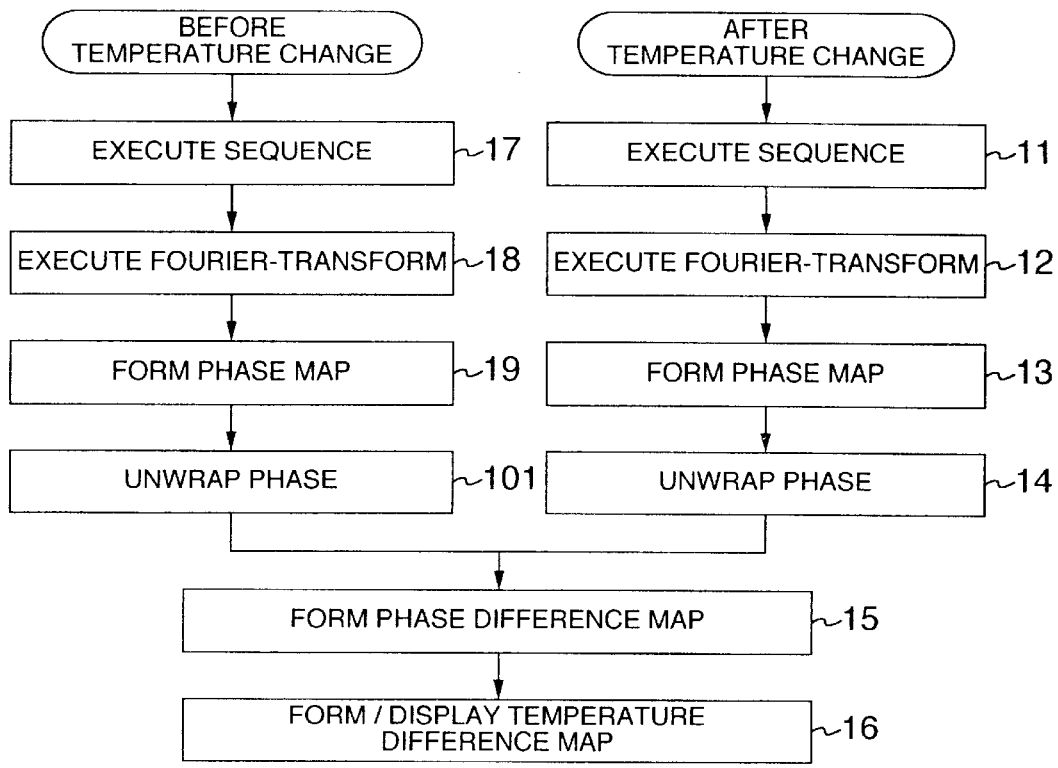
FIG. 1 is a diagram for representing a sequence of measuring a temperature distribution in an MRI apparatus of the present invention.

FIG. 1 is a diagram for indicating a sequential operation of a temperature measurement. This temperature measurement is carried out at least two times under such conditions that before the laser ablation is carried out, namely before a temperature change occurs, the temperature measurement is performed; and while the laser ablation is carried out, or after the laser ablation has been carried out, a temperature change occurs under which the temperature measurement is carried out. Each of the temperature measurements is constituted by a data measurement (17, 11) by executing an imaging sequence, a Fourier transform of measurement data (18, 12), a formation of a phase map (19, 13), and a phase unwrap process (101, 14).

Furthermore, a phase difference map is produced (15) from phase maps which are obtained by executing the two temperature measurements, and a temperature difference map is produced from these maps to be displayed (16).

Figure 2:
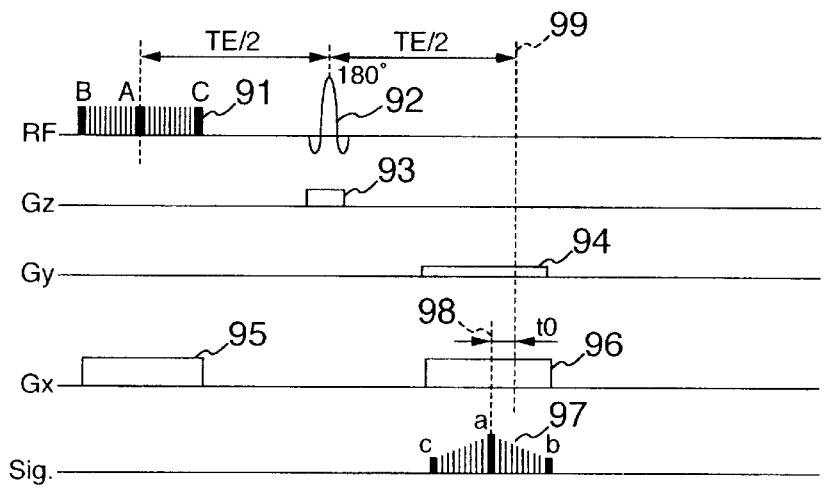
FIG. 2 is a diagram for indicating an embodiment of an imaging sequence employed in the MRI apparatus of the present invention.

FIG. 2 shows an example of an imaging sequence executed at steps (17, 11). In this drawing, symbol "RF" indicates radio-frequency magnetic field pulse, symbols Gz, Gy, Gx represent gradient magnetic field pulses along three directions located perpendicular to each other, and symbol "Sig" denotes echo signals. In this embodiment, it is so assumed that symbol "Gz" is a gradient magnetic field along a slice direction, symbol "Gy" is a gradient magnetic field along a phase encode direction, and symbol "Gx" is a gradient magnetic field along a readout direction.

Figure 3A:
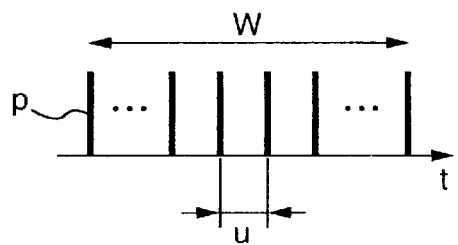
FIG. 3A and FIG. 3B are diagrams for representing burst waves employed in the imaging sequence of FIG. 2.

In this imaging sequence, magnetization is excited by an RF burst 91 in the beginning. At the same time, the gradient magnetic field Gx95 of the readout direction is applied. As represented in FIG. 3A, the RF burst 91 corresponds to a series of RF pulses which are constituted by a plurality of sub-pulses "p", and an amplitude of a sub-pulse "p" is set in such a manner that a flip angle by the entire burst becomes 90 degrees. As indicated in FIG. 3C, only magnetization of such a stripe-shaped region 301 in the x direction is excited by such an RF burst 91 and the gradient magnetic field Gx95. For example, assuming now that the width of the sub-pulse of the RF burst is equal to 200 μs, an interval of a sub-pulse on a frequency axis is equal to 1/(200 μs)=5 KHz. Assuming now that a strength of the gradient magnetic field Gx which is simultaneously applied with the RF pulse is equal to 23.3 mT/m, it becomes γ×(5 mm)×Gx=5 KHz, so that the magnetization is excited in the interval of 5 mm along the x direction.

Next, an inverting. (180 degrees) RF pulse 92 is applied after TE/2 has passed from a center position of the burst wave 91. The gradient magnetic field Gz93 is applied at the same time when this inverting RF pulse 92 is applied so as to select a slice. After the inverting RF pulse 92 has been applied, while a gradient magnetic field Gx96 along the readout direction is applied so as to measure a signal. This gradient magnetic field Gx96 has the same code as that of the gradient magnetic field Gx95 which is applied when the transverse magnetization is excited. The magnetization within the stripe-shaped region 301 (FIG. 3C), the phases of which are distributed by the gradient magnetic fields Gx95 when the magnetization is excited, are again converged by applying the gradient magnetic field Gx96 along the readout direction, so that gradient magnetic echoes 97 having the same number as a total number of the sub-pulses contained in the burst wave are produced. At the same time, another gradient magnetic field pulse Gy94 having a constant amplitude is applied so as to apply different phase encodes to the respective echoes. As a result, while the sequence is carried out one time, it is possible to obtain data for 1 slice in which a sampling number x a pixel number (stripe number) along the readout direction are used as a matrix.

At this time, since the inverting RF pulse 92 is applied, the magnetization is inverted, and spin echoes are produced at a time instant 99 after TE/2 has elapsed since this inverting RF pulse 92 was applied. The application timing of the readout gradient magnetic field Gx96 is set in such a manner that a time instant 98 when a central echo of the gradient magnetic field echo 9 is shifted by time "t0" from a time instant 99 when the spin echo is produced. Also, since the sign of the gradient magnetic field Gx95 is the same as that of the gradient magnetic field Gx96, as to the echoes corresponding to the respective sub-pulses of the burst wave, the generation orders thereof are reversed. In other words, since the magnetization is reconverged by the gradient magnetic field Gx96 having the same operation amount as the operation amount of the gradient magnetic field Gx95, the sub-pulses A, B, and C of FIG. 2 correspond to echoes "a", "b", and "c."

As explained above, since both the application timing and the sign of this readout gradient magnetic field Gx96 are controlled, the respective echoes are produced having the time difference of "t0" with respect to the spin echo time instants. As a result, the phase rotation which is proportional to both a static magnetic field ununiformity Es (x, y) containing a chemical shift and the time difference "t0" is given to the respective echoes. As a consequence, since these echo signals are Fourier-transformed, a phase image of a selected slice plane can be obtained (steps 18, 12).

This fact will now be explained based upon the below-mentioned formulae (3) and (4). That is to say, the respective echoes are expressed by the following formula (3). The phase component is expressed by a term "exp" of an imaginary factor.

$$S(t,\ G_y)=\int\int \rho(x,y)\exp[i\gamma(G_y t_y y+G_x tx+(t-t_0)\ Es(x,y))]dxdy=\int\int \rho(x,y)\exp[i\gamma(G_y t_y y+G_x(x+Es(x,y)/G_x)t-t_0 Es(x,y))]dxdy \quad (3)$$

In this formula(3), symbol "ρ" is a proton density, symbol "ty" represents an echo interval, and symbol "t" denotes time measured from an echo center, which is defined for each echo.

In the second formula of the above-explained formula (3), in such a case that Es (x, y)/Gx is negligible as compared with "x", this formula (3) may be approximated by the following formula (4)

$$S(t,\ G_y)=\int\int \rho(x,y)\exp(-i\gamma t_0 Es(x,y))\exp i\gamma(G_y t_y y+G_x x\ t)dxdy \quad (4)$$

The signal S (t, Gy) is Fourier-transformed from the formula (4), to obtain p (x, y) exp (--iγytoEs (x, y)). That is, it can be seen that such a density distribution containing the phase rotation which is proportional to T0×Es (x, y) can be acquired.

A phase map is obtained in such a manner that a measurement signal (complex number) which is quadrature-detected is Fourier-transformed, and then, arctan (imaginary part/real part) having a sign is calculated from both a real part and an imaginary part of a pixel value (steps 19, 13 of FIG. 1). The resulting phase map (phase image) is illustratively indicated in FIG. 5. It should be noted that in FIG. 5, a region 27 corresponds to such a portion, the temperature of which is increased by a laser ablation and the like. The phase of this region is largely changed due to temperature changes, as compared with a peripheral region.

Figure 5:
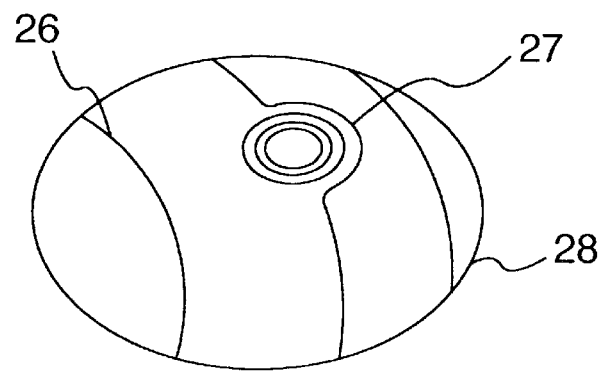
FIG. 5 is a diagram for schematically showing a phase map acquired by the MRI apparatus of the present invention.

As represented by a line 26 of FIG. 5 where the phase thereof jumps by 2π, since the arctan calculation is carried out, the phase is folded every 2π radians, and the therefore, the correct temperature change cannot be calculated directly from this phase map. As a result, a phase unwrap process operation is carried out (steps 101, 14 of FIG. 1). As the phase unwrap processing method, for example, such a method may be employed. That is, while a reference point (x0, y0) of the phase map is determined, the phase unwrap process operation is commenced from the phase reference point. In such a case that there is a change larger than, or equal to $2\pi$ in the adjoining pixels, this change is reduced by adding/subtracting $2\pi$.

In other words, while ($2\pi+\alpha$) is handled as "$\alpha$", the phase unwrap process is carried out.

Next, a temperature map is produced from the phase map. As previously explained, the sequential operations defined by the execution of the imaging sequence, the Fourier-transform of the measurement data, the formation of the phase map, and the phase unwrap process operation have been carried out at least two times before and after the temperature change (otherwise while temperature change). As a consequence, a difference between these phase maps obtained in the above operations is calculated, and then, a phase difference map $\Delta\emptyset(x,y)$ is formed by this phase map difference (step 15 of FIG. 1). A temperature difference map $\Delta T(x,y)$ is produced by way of the calculation as to this phase difference map (step 16).

A calculation used to form a temperature difference from a phase difference is carried out as follows:

In the formula (4) indicative of the echo signal, in the case that such a static magnetic field ununiformity Es(x,y) which may apply a rotation to this phase depends upon only a temperature change in proton chemical shifts, this static magnetic field ununiformity Es(x,y) is expressed by the below-mentioned formula (5):

$$Es(x,y)=B_0\Delta\delta \quad (5)$$

In this formula (5), symbol "$\Delta\delta$" shows a change caused by temperatures of chemical shifts, and symbol "$B_0$" indicates a strength of a static magnetic field.

As a consequence, a phase change "$\Delta\emptyset$" caused by the static magnetic field ununiformity Es(x,y) may be expressed by the following formula (6):

$$\Delta\phi=\gamma t_0 E_s(x,y)=\gamma t_0 B_0 \Delta\delta \quad (6)$$

On the other hand, since a temperature change "$\Delta T$" is defined as $\Delta T=\Delta\delta/\alpha$ ("$\alpha$" indicates the temperature dependent characteristic [0.001 ppm/°C.] the chemical shift of water proton) from the above-explained formulae (1) and (2), the temperature change $\Delta T$ may be calculated from the phase change $\Delta\emptyset$ of the formula (6) may be calculated by the following formula (7):

$$\Delta T = \frac{\Delta\delta}{\alpha} = \frac{\Delta\phi}{\alpha\gamma t_0 B_0} \quad (7)$$

Thus, the temperature difference map obtained in this manner is displayed on the CRT display (step 16). As to the display of the temperature difference, this temperature difference may be preferably displayed on a previously acquired tissue image in a superimpose manner. Also, as a method of displaying the temperature difference map, for example, while such a color bar is prepared in which an arbitrary color is allocated every predetermined temperature width, a temperature of a certain pixel is indicated by a color corresponding to a temperature of this color bar. For instance, temperatures of 30° C. to 200° C. are allocated in the unit of 10° C. to such a color bar, the color hue of which is successively changed such as blue-green-yellow-orange-red. When a temperature of a certain pixel is equal to 100° C. (otherwise, a difference between this temperature and a temperature before temperature change is 74° C.), a color of this color bar corresponding to this temperature (temperature difference), for instance, the orange color is displayed by being superimposed with luminance of the pixel.

As the display method of the temperature, in addition to the above-explained color display, such methods may be employed. That is, an isocolor-temperature contour, gradation in the same color hue may be employed. In any of these temperature display method, these temperatures are preferably displayed with being superimposed on the tissue images. As a result, it is possible to confirm such a portion that the temperature change occurs.

As previously described, in this embodiment, while the highspeed sequence with employment of the burst wave is employed as the imaging sequence and also the gradient magnetic field echoes are produced at the different time instants from those of the spin echoes, these gradient magnetic field echoes can be measured and processed to produce the two-dimensional phase map within a shorten time period than, or equal to 0.1 second. As a consequence, while the IVMR imaging is carried out, the two-dimensional temperature may can be measured and displayed in substantially real time.

Figure 6:
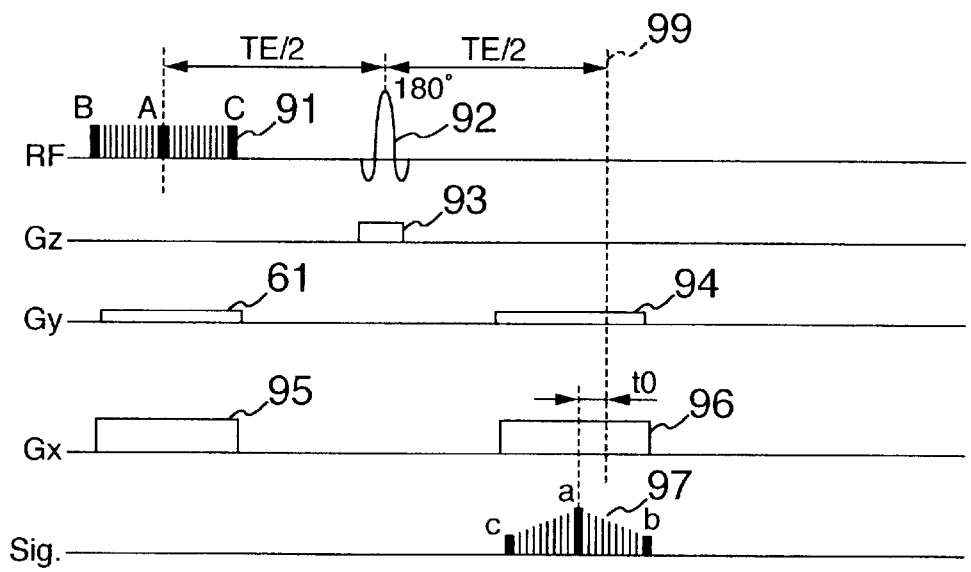
FIG. 6 is a diagram for representing another embodiment of an imaging sequence employed in the MRI apparatus of the present invention.

It should be understood that in the above-explained embodiment, as the imaging sequence, such a sequence is indicated in which the gradient magnetic field Gy94 of the phase encode is applied while the echoes are measured. Alternatively, as represented in FIG. 6, the phase encode Gy61 may be carried out when the transverse magnetization is excited. In this alternative case, a similar effect to that of the embodiment shown in FIG. 2 may be achieved. The sequence shown in FIG. 6 is similar to the sequence of FIG. 2 except for such timing when the phase-encode.

In the embodiment above mentioned, the case of 2-dimentional measurement is explained. However, by adding a phase encode loop in a slice direction, a 3-dimensional measurement can be carried out.

Figure 7:
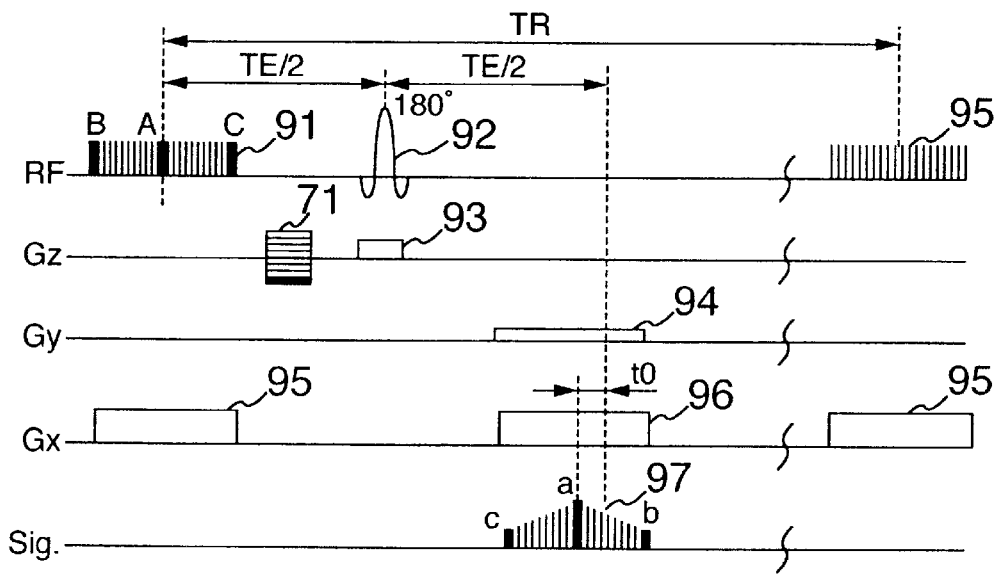
FIG. 7 is a diagram for representing another embodiment of an imaging sequence employed in the MRI apparatus of the present invention.

As a second embodiment, a sequence of a 3-dimensional measurement is represented in FIG. 7. This sequence is basically identical to the sequence indicated in FIG. 2, in which the same pulses are denoted by the same numbers of FIG. 2. It should be noted that in the sequence shown in FIG. 7, a phase-encoding gradient magnetic field Gz71 along a slice direction is applied between a burst wave 91 and an inverting RF pulse 92. Also, a gradient magnetic field Gz93 which is applied in combination with the inverting RF pulse 92 corresponds to such a gradient magnetic field which is used to select a region (slab) containing an entire slice which will be measured.

While a strength of the phase-encoding gradient magnetic field Gz71 along the slice direction is changed, this sequence is repeatedly carried out in repetition time "TR", so that 3-dimensional measurement data is acquired. Similar to the case of the 2-dimensional measurement, this 3-dimensional measurement data corresponds to such data having a phase sensitivity. Since this 3-dimensional measurement data is processed by way of the 3-dimensional Fourier-transform, a 3-dimensional phase map can be obtained.

Similar to the case of the 2-dimensional measurement, also in this 3-dimensional measurement, a phase difference map and a temperature difference map are formed from the acquired 3-dimensional phase map, and then, a temperature is displayed.

In general, while a measurement is carried out by using a burst wave, since a slice selection cannot be performed during excitation, an inverting RF pulse owns a slice selective characteristic. However, in accordance with the sequence of the present invention, since a gradient magnetic field echo is basically produced, a slice selection cannot be realized. As a consequence, such a 3-dimensional measurement to which the phase encode Gz along the slice direction is added may become effective. Even when the 3-dimensional measurement is carried out, since a measurement of one excitation cycle becomes very short time (on the order of 0.1 second) and also a phase-encode step number along the slice direction becomes relatively small, for instance, approximately 16 steps, it is possible to realize such a short time measurement which can be fitted to the purpose of IVMR.

It should also be understood that in the above-explained descriptions, the sequence is repeatedly carried out in the repetition time TR after waiting for the recovery time of the longitudinal magnetization. Alternatively, if the carrier frequency of the excitation-purpose burst 91 is shifted every excitation operation and then the region to be excited (301 of FIG. 3C) is shifted so as to excite such unexcited longitudinal magnetization, then such a repetition time "TR" may be set which is shorter than the normal longitudinal relaxation time T1.

In other words, as previously explained, the magnetization which is excited by applying the gradient magnetic field Gx95 along the readout direction at the same time when the RF burst 91 is applied corresponds to the magnetization of the strip-shaped region 301 along the x direction as indicated in FIG. 3C. As a result, the magnetization existed in the region 302 between the regions 301 is not yet excited, while shifting the frequency of the burst, this magnetization may be excited. For instance, this frequency is shifted only by 1/(u×pixel number along readout direction) (Hz) every excitation operation.

As explained above, while the frequency of the burst 91 is sequentially shifted, the sequence is repeatedly carried out in short repetition time so as to sequentially excite and measure the new regions. Then, after the longitudinal relaxation time T1 of the firstly excited region has passed, the present frequency is returned to such a frequency which is used to first select this region, and then, the phase encode step is incremented. Subsequently, while the frequency of the burst 91 is sequentially shifted, the sequence is repeatedly carried out, and thus, all of the phase encode step is accomplished. As a consequence, while the imaging time is not increased, or is minimized, the spatial resolution along the slice direction may be increased.

Assuming now that in this 3-dimensional measurement, for example, the echo time TE=40 ms, the repetition time TR=60 ms, and the phase step number along the slice direction (pixel number along slice direction) is equal to 16, the 3-dimensional measurement can be accomplished within approximately 1 second.

It should also be noted that this method for shifting the carrier frequency of the burst 91 every excitation operation may be applied not only to the 3-dimensional measurement, but also to the 2-dimensional measurement. However, in such a measurement case that such a sequence is repeatedly carried out, since the direction of the unexcited longitudinal magnetization is changed along the +z direction or the −z direction every cycle by the inverting pulse 92, such an attention should be paid as to invert the phase.

Figure 8:
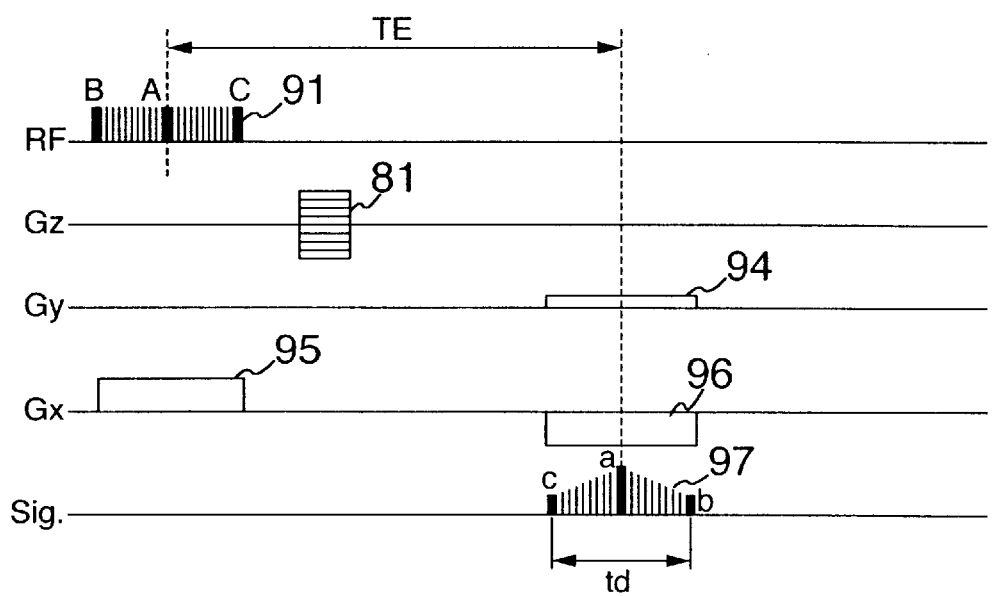
FIG. 8 is a diagram for representing another embodiment of an imaging sequence employed in the MRI apparatus of the present invention.

Next, as a third embodiment of the present invention, such a sequence without employing an inverting RF pulse is explained with reference to FIG. 8. In this sequence which is different from the above-explained sequences of FIG. 2, FIG. 6, and FIG. 7, a gradient magnetic field echo 97 is produced without using an inverting RF pulse 92. In this case, since the slice selection by the inverting RF pulse 92 is not carried out, a phase-encode gradient magnetic field 81 is applied along the slice direction. While a strength of this phase-encode gradient magnetic field 81 is changed, the cycle is repeatedly carried out in repetition time TR so as to perform a 3-dimensional measurement.

In this sequence, since the longitudinal magnetization is not inverted by applying the inverting RF pulse 92, the readout gradient magnetic field Gx96 owns a different sign from that of the gradient magnetic field Gx95 which is applied at the same time when the burst wave 91 is applied. Also, in principle, since no spin echo is produced, the echo time TE may be arbitrarily set. Since a phase of a spin is changed in proportional to this echo time TE, the phase sensitivity may be increased by setting the echo time TE to be long. It should also be noted that when observing the respective echoes which constitute an echo stream 97, time defined by that the excitation RF pulse 91 is applied until these echoes are produced may differ from each other, so that the echo time TE may become different from each other along a ky-axial direction on a k-space (phase space). However, if an entire length of this echo stream 97 is shorter than the effective TE (namely, TE of central echo "a"), namely if TE>>td, then the differences in TEs of the respective echoes may be negligible.

As a consequence, the same effect as that of FIG. 7 can be achieved.

Also, in this embodiment, the phase encode operation along the Gy direction may be carried out in any one of such cases that the longitudinal magnetization is excited, and the echo is measured. Also, since the carrier frequency of the excitation burst is shifted every excitation operation so as to excite the unexcited longitudinal magnetization, the repetition time TR may be made shorter than the normal longitudinal relaxation time T1.

Figure 3B:
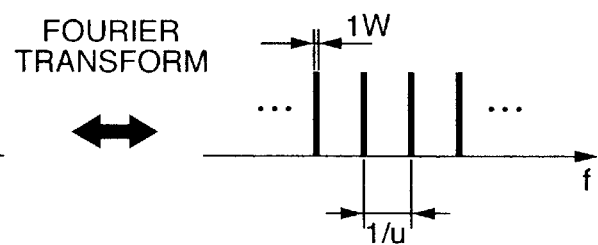
Figure 3C:
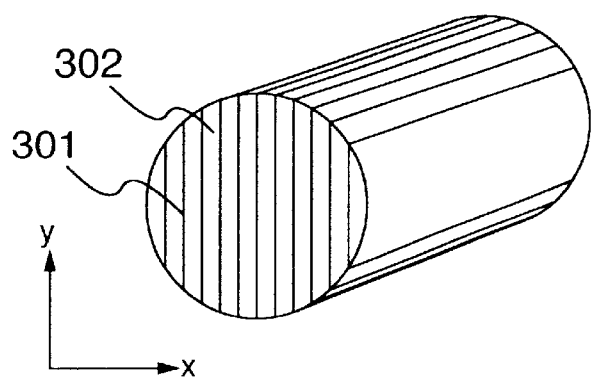
FIG. 3C is a diagram for showing a region which is excited by the burst waves.

As the burst waves employed in the present invention, various modified burst pulses may be employed instead of the pulse streams having the constant amplitudes as represented in FIG. 3A and FIG. 3B. For example, such a technique capable of improving a signal strength may be combined with the present invention, by which while an excitation burst wave is properly modulated by way of either a frequency modulation or an amplitude modulation, a width of a pulse of an excitation spectrum is widened.

Also, in the present invention, only the phase distribution may be utilized.

In the case that a folding phenomenon of a phase occurs, a temperature cannot be correctly measured. However, if a time difference before and after such a temperature change is small, then a phase change becomes smaller than, or equal to $2\pi$, so that fold back of the phase never occurs. In such a case, the phase distribution obtained before the phase distribution is converted into the temperature distribution may also be used so as to monitor the temperature.

Also, as another embodiment of the present invention, under such a condition that both a static magnetic field distribution and a chemical shift may be negligible, a difference before/after a temperature change need not be calculated. In this case, a phase map obtained when no temperature changes becomes substantially flat. While a proportional relationship between a phase change amount and a temperature change amount is previously measured, a temperature may be directly measured from a value of a phase. In this case, symbol "$\Delta\delta$" contained in the formula (1) represents a change amount of a chemical shift which is caused by a temperature change from an environment temperature under which an object under examination is located.

In this case, a phase map is acquired by executing the steps 17, 18, 19, and 101, or the steps 11, 12, 13, and 14 of the sequence shown in FIG. 1. Then, an image indicative of a temperature change is formed from this phase map, and thus, the image may be displayed.

The present invention is not limited only to the above-explained embodiments, but may cover various modifications which are defined by the technical scope and spirit of the pending claims.

Industrial Applicability

A medical MRI apparatus and an analysis MRI apparatus are realized which are suitably used to measure a temperature distribution of an object under examination.

What is claimed is:

1. A magnetic resonance image diagnosing apparatus comprising: magnetic field generating means for generating a static magnetic field, a gradient magnetic field, and a radio-frequency magnetic field in a space where an object under examination is located; detecting means for detecting a magnetic resonance signal produced from said object under examination; means for reconstructing an image based upon said detected magnetic resonance signal; display means for displaying thereon an image; and control means for controlling each of said means, wherein:
said control means executes the below-mentioned sequences, namely:
1) a burst wave for exciting nuclei of hydrogen is applied as said radio-frequency magnetic field, and at the same time, a gradient magnetic field along at least one direction is applied;
2) after said burst wave has been applied, a magnetization-inverting radio-frequency pulse is applied in combination with a slice-selecting gradient magnetic field;
3) a readout-operating gradient magnetic field is applied in such a manner that a gradient magnetic field echo is produced at such a time instant different from a time instant when a spin echo is produced by applying said radio-frequency pulse;
4) when said burst wave is applied, or said magnetic resonance signal is detected, such a gradient magnetic field which phase-encodes said magnetic resonance signal is applied;
5) the phase-encoded magnetic resonance signal is detected as the gradient magnetic field echo;
6) said detected magnetic resonance signal is Fourier-transformed, and a phase distribution is calculated based upon both a real part and an imaginary part of complex data of the Fourier-transformed magnetic resonance signal; and
7) an image is constructed from said phase distribution, and said constructed image is displayed on said display means.

2. A magnetic resonance image diagnosing apparatus as claimed in claim 1 wherein:
when said control means constructs the image from said phase distribution, a temperature distribution calculated from said phase distribution is constructed as the image.

3. A magnetic resonance image diagnosing apparatus as claimed in claim 1 wherein:
after said burst wave has been applied, said control means applies a gradient magnetic field for phase-encoding the magnetic resonance signal along a slice direction; while a strength of said gradient magnetic field is changed, said control means repeatedly executes said sequences 1) to 5); and said control means processes the acquired data by way of a 3-dimensional Fourier-transform to thereby form a 3-dimensional phase distribution.

4. A magnetic resonance image diagnosing apparatus as claimed in claim 3 wherein:
every time said control means repeatedly executes the phase encoding operation of said slice direction, said control means changes a frequency of said burst wave so as to sequentially excite different regions, and to repeatedly execute said sequences 1) to 5) in repetition time shorter than longitudinal magnetization recovery time.

5. A magnetic resonance image diagnosing apparatus as claimed in claim 1 wherein:
said control means executes said sequences 1) to 5) two times, or more at different time instants; every time said sequences 1) to 5) are carried out, said control means acquires a phase distribution; and said control means calculates a difference among these phase distributions, and then converts said calculated difference into a temperature change so as to display said temperature change.

6. A magnetic resonance image diagnosing apparatus comprising: magnetic field generating means for generating a static magnetic field, a gradient magnetic field, and a radio-frequency magnetic field in a space where an object under examination is located; detecting means for detecting a magnetic resonance signal produced from said object under examination; means for reconstructing an image based upon said detected magnetic resonance signal; display means for displaying thereon an image; and control means for controlling each of said means, wherein:
said control means executes the below-mentioned sequences, namely:
1) a burst wave for exciting nuclei of hydrogen is applied as said radio-frequency magnetic field, and at the same time, the gradient magnetic field along at least one direction among three directions is applied;
2) while a gradient magnetic field having a polarity opposite to that of said gradient magnetic field is applied as a readout-operating gradient magnetic field, a magnetic resonance signal is detected as a gradient magnetic field echo;
3) said detected magnetic resonance signal is Fourier-transformed, and a phase distribution is calculated based upon both a real part and an imaginary part of complex data of the Fourier-transformed magnetic resonance signal; and
4) an image is constructed from said phase distribution, and said constructed image is displayed on said display means.

7. A magnetic resonance image diagnosing apparatus as claimed in claim 6 wherein:
when said control means constructs the image from said phase distribution, a temperature distribution calculated from said phase distribution is constructed as the image.

8. A magnetic resonance image diagnosing apparatus as claimed in claim 6 wherein:
after said burst wave has been applied, said control means applies a gradient magnetic field for phase-encoding the magnetic resonance signal along a slice direction; while a strength of said gradient magnetic field is changed, said control means repeatedly executes said sequences 1) and 2); and said control means processes the acquired data by way of a 3-dimensional Fourier-transform to thereby form a 3-dimensional phase distribution.

9. A magnetic resonance image diagnosing apparatus as claimed in claim 8 wherein:

every time said control means repeatedly executes the phase encoding operation of said slice direction, said control means changes a frequency of said burst wave so as to sequentially excite different regions, and to repeatedly execute said sequences 1) and 2) in repetition time shorter than longitudinal magnetization recovery time.

10. A magnetic resonance image diagnosing apparatus as claimed in claim 6 wherein:

said control means executes said sequences 1) and 2) two times, or more at different time instants; every time said sequences 1) and 2) are carried out, said control means acquires a phase distribution; and said control means calculates a difference among these phase distributions, and then converts said calculated difference into a temperature change so as to display said temperature change.

11. In a magnetic resonance image diagnosing apparatus comprising: magnetic field generating means for generating a static magnetic field, a gradient magnetic field, and a radio-frequency magnetic field in a space where an object under examination is located; detecting means for detecting a magnetic resonance signal produced from said object under examination; means for reconstructing an image based upon said detected magnetic resonance signal; display means for displaying thereon an image; and control means for controlling each of said means, said magnetic resonance image diagnosing apparatus is comprised of:

means for applying a burst wave to said object under examination so as to excite a predetermined region of said object under examination;

means for detecting a magnetic resonance signal produced by said burst wave as a gradient magnetic echo;

means for Fourier-transforming the detected magnetic resonance signal and for acquiring a phase distribution from complex data of the Fourier-transformed magnetic resonance signal; and means for constructing an image from said phase distribution.

12. A magnetic resonance image diagnosing apparatus as claimed in claim 11 wherein:

said image constructing means includes means for constituting a temperature distribution acquired from said phase distribution as an image.

13. A magnetic resonance image diagnosing apparatus as claimed in claim 11 wherein:

said magnetic resonance image diagnosing apparatus is further comprised of:

means for applying a gradient magnetic field used to phase-encode the magnetic resonance signal along a slice direction, and for detecting said magnetic resonance signal while changing a strength of said gradient magnetic field; and said phase distribution acquiring means includes means for performing a 3-dimensional Fourier transform with respect to the acquired data so as to form a 3-dimensional phase distribution.

14. A magnetic resonance image diagnosing apparatus as claimed in claim 13 wherein:

said means for exciting the object under examination includes means operated in such a manner that every time the phase encode operation along the slice direction is repeatedly carried out, a frequency of said burst wave is changed so as to sequentially excite different regions; and said magnetic resonance image diagnosing apparatus is further comprised of means for detecting said gradient magnetic echo in repetition time shorter than longitudinal magnetization recovery time.

15. A magnetic resonance image diagnosing apparatus as claimed in claim 11 wherein:

said magnetic resonance image diagnosing apparatus is further comprised of means for performing a sequence used to detect said gradient magnetic echo at different time instants two times, or more;

said phase distribution acquiring means includes means for acquiring a phase distribution every time said sequence is carried out; and said image displaying means includes means for calculating a difference among said plurality of phase distributions and for converting said calculated difference into a temperature change to display said temperature change.

16. An MR imaging method realized in a magnetic resonance image diagnosing apparatus comprising: magnetic field generating means for generating a static magnetic field, a gradient magnetic field, and a radio-frequency magnetic field in a space where an object under examination is located; detecting means for detecting a magnetic resonance signal produced from said object under examination; means for reconstructing an image based upon said detected magnetic resonance signal; display means for displaying thereon an image; and control means for controlling each of said means, wherein:

said MR imaging method is comprised of:

1) a step in which a burst wave for exciting nuclei of hydrogen is applied as said radio-frequency magnetic field, and at the same time, a gradient magnetic field along at least one direction is applied;

2) a step in which after said burst wave has been applied, a magnetization-inverting radio-frequency pulse is applied in combination with a slice-selecting gradient magnetic field;

3) a step in which a readout-operating gradient magnetic field is applied in such a manner that a gradient magnetic field echo is produced at such a time instant different from a time instant when a spin echo is produced by applying said radio-frequency pulse;

4) a step in which when said burst wave is applied, or said magnetic resonance signal is detected, such a gradient magnetic field which phase-encodes said magnetic resonance signal is applied;

5) a step in which the phase-encoded magnetic resonance signal is detected as the gradient magnetic field echo;

6) a step in which said detected magnetic resonance signal is Fourier-transformed, and a phase distribution is calculated based upon both a real part and an imaginary part of complex data of the Fourier-transformed transformed magnetic resonance signal; and 7) a step in which an image is constructed from said phase distribution, and said constructed image is displayed on said display means.

17. An MR imaging method as claimed in claim 16 wherein:

said image displaying step includes a step for constructing the temperature distribution acquired from said phase distribution as an image.

18. An MR imaging method as claimed in claim 16, further comprising:

a step in which after said burst wave has been applied, a gradient magnetic field for phase-encoding the magnetic resonance signal along a slice direction is applied; and a step in which while a strength of said gradient magnetic field is changed, said steps 1) to 5) are repeatedly executed; and wherein:

said phase distribution calculating step includes a step for performing a 3-dimensional Fourier-transform with respect to the acquired data so as to form a 3-dimensional phase distribution.

19. An MR imaging method as claimed in claim 18, further comprising:

a step in which every time the phase encoding operation of said slice direction is repeatedly executed, a frequency of said burst wave is changed so as to sequentially excite different regions; and a step for repeatedly executing said steps 1) to 5) in repetition time shorter than longitudinal magnetization recovery time.

20. An MR imaging method as claimed in claim 16, further comprising:

a step for executing said steps 1) to 5) at different time instants two times, or more; and wherein:

said phase distribution calculating step includes a step for calculating a phase distribution every time said steps 1) to 5) are executed; and said image displaying step includes a step for calculating a difference among these phase distributions, and for converting said difference into a temperature change so as to display said temperature change.

21. An MR imaging method as claimed in claim 20, further comprising:

a step for executing said steps 1) and 2) at different time instants two times, or more; and wherein:

said phase distribution calculating step includes a step for calculating a phase distribution every time said steps 1) and 2) are executed; and said image displaying step includes a step for calculating a difference among these phase distributions, and for converting said difference into a temperature change so as to display said temperature change.

22. An MR imaging method realized in a magnetic resonance image diagnosing apparatus comprising: magnetic field generating means for generating a static magnetic field, a gradient magnetic field, and a radio-frequency magnetic field in a space where an object under examination is located; detecting means for detecting a magnetic resonance signal produced from said object under examination; means for reconstructing an image based upon said detected magnetic resonance signal; display means for displaying thereon an image; and control means for controlling each of said means, wherein:

said MR imaging method is comprised of:

1) a step in which a burst wave for exciting nuclei of hydrogen is applied as said radio-frequency magnetic field, and at the same time, the gradient magnetic field along at least one direction among three directions is applied;

2) a step in which while a gradient magnetic field having a polarity opposite to that of said gradient magnetic field is applied as a readout-operating gradient magnetic field, a magnetic resonance signal is detected as a gradient magnetic field echo;

3) a step in which said detected magnetic resonance signal is Fourier-transformed, and a phase distribution is calculated based upon both a real part and an imaginary part of complex data of the Fourier-transformed magnetic resonance signal; and 4) a step in which an image is constructed from said phase distribution, and said constructed image is displayed on said display means.

23. An MR imaging method as claimed in claim 22 wherein:

said image displaying step includes a step for constructing the temperature distribution acquired from said phase distribution as an image.

24. An MR imaging method as claimed in claim 22, further comprising:

a step in which after said burst wave has been applied, a gradient magnetic field for phase-encoding the magnetic resonance signal along a slice direction is applied;

a step in which while a strength of said gradient magnetic field is changed, said steps 1) and 2) are repeatedly executed; and wherein:

said phase distribution calculating step includes a step for performing a 3-dimensional Fourier-transform with respect to the acquired data so as to form a 3-dimensional phase distribution.

25. An MR imaging method as claimed in claim 24, further comprising:

a step in which every time the phase encoding operation of said slice direction is repeatedly executed, a frequency of said burst wave is changed so as to sequentially excite different regions; and a step for repeatedly executing said steps 1) and 2) in repetition time shorter than longitudinal magnetization recovery time.

\* \* \* \* \*